United States Patent [19]

Cook et al.

[11] Patent Number: 4,890,623

[45] Date of Patent: Jan. 2, 1990

[54] BIOPOTENTIAL SENSING DEVICE AND METHOD FOR MAKING

[75] Inventors: William Cook, Billerica; Jack Herman, Andover; Donald Rowe, Lowell; John Sylvanowicz, Andover, all of Mass.

[73] Assignee: C. R. Bard, Inc., Murray Hill, N.J.

[21] Appl. No.: 167,878

[22] Filed: Mar. 14, 1988

[51] Int. Cl.[4] .............................................. A61B 5/04
[52] U.S. Cl. ................................... 128/642; 128/786; 29/831
[58] Field of Search ........................ 128/642, 635–641, 128/784–786, 419 P; 29/831

[56] References Cited

U.S. PATENT DOCUMENTS

| | | | |
|---|---|---|---|
| 3,707,960 | 1/1973 | Freed | 128/1 |
| 4,317,278 | 3/1982 | Carmon et al. | 128/639 |
| 4,461,304 | 7/1984 | Kuperstein | 128/642 |
| 4,640,289 | 2/1987 | Craighead | 128/639 |
| 4,762,135 | 8/1988 | Puije | 128/784 |

FOREIGN PATENT DOCUMENTS

| | | |
|---|---|---|
| 6175700 | 4/1986 | Japan. |
| 6227991 | 1/1987 | Japan. |
| 8707825 | 12/1987 | PCT Int'l Appl. ................ 128/784 |
| 2185403 | 7/1987 | United Kingdom. |

OTHER PUBLICATIONS

Pochay et al, "A Multichannel Depth Probe . . . ", IEEE Trans. Biomed. Eng. vol. BME-26, No. 4, Apr. 1979, pp. 199–206.
Christopher R. C. Wyndham, M. D.; Matthew Prucka, B.S.E.E.; Huang-Ta Lin M. D.; Jeffrey Lacy, Ph. D.; Baylor College of Medicines, Houston, Texas–"Portable Computerized Cardiac Intraoperative Mapping Using a New Technology Electrode Array"–Abstract for Engineering Foundation Meeting: Apr. 5–10, 1986.
"Flexible Printed–Circuit Probe for Electrophysiology", R. S. Pickard, P. L. Joseph, A. J. Collins & R. C. J. Hicks–Medical & Biological Engineering & Computing, Mar. 1979, pp. 261–267.
Technical Note–"The Shape Conforming Electrode", Medical & Biological Engineering, vol. 7, pp. 341–343; Pergamon Press, 1969, printed in Great Britain.
Martin Sonn & Wolfgang M. Feist, A Prototype Flexible Microelectrode Array for Implant–Prosthesis Applications, Medical & Biological Engineering, Nov. 1974, pp. 778–790.
R. S. Pickard & T. R. Welberry, Printed Circuit Microelectrodes and Their Application to Honeybee Brain, Department of Zoology and Department of Physics, University College, Cardiff, Wales CF1 1XL, pp. 39–44.

Primary Examiner—Lee S. Cohen
Attorney, Agent, or Firm—Wolf, Greenfield & Sacks

[57] ABSTRACT

A printed circuit biopotential sensing device is provided which is particularly adapted for endocardial or other deep body applications. The device has a predetermined printed circuit pattern formed on a thin film substrate, the pattern having at least one electrode pad at its distal end, at least one terminal pad at the proximal end, and conductor means selectively interconnecting the electrode pads and terminal pads. The substrate is secured to, and is preferably wrapped around an elongated member which is preferably tube-shaped in a manner such that the electrodes are exposed at the distal end of the member, and the terminal pads at the proximal end of the substrate are utilized in forming a suitable connector from the device. By forming the conductors on only a selected fraction of the width of the substrate and overlapping the portion of the substrate containing the conductors during the helical wrapping process, the substrate insulates and protects the conductors and eliminates the need for a separate protective layer. The device may, for example, be a percutaneous catheter with the electrodes being formed at the distal end thereof, or may be a sensing probe which includes a sensing support member, such as a solid plastic member or a balloon which has the distal end of the substrate containing the electrode pads secured thereto.

24 Claims, 3 Drawing Sheets

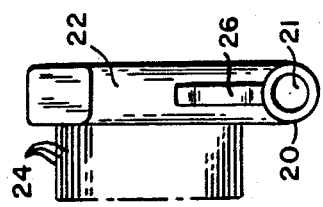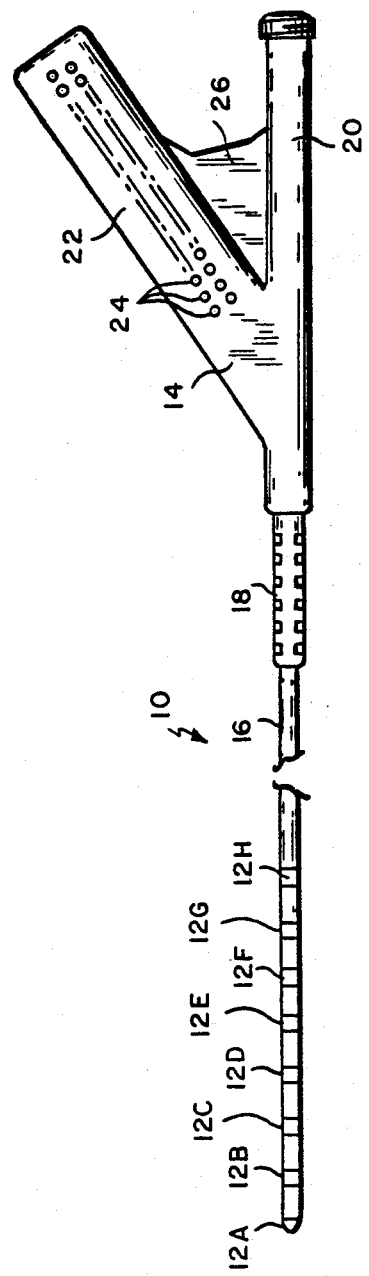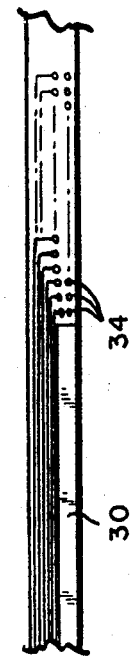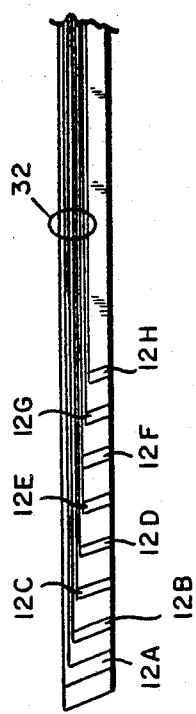

BIOPOTENTIAL SENSING DEVICE AND METHOD FOR MAKING

FIELD OF THE INVENTION

This invention relates to devices for sensing biopotentials and, more particularly, to biopotential sensing devices utilizing printed circuit technology.

BACKGROUND OF THE INVENTION

There are many situations where, for diagnostic purposes, for monitoring purposes during surgery or other medical procedures, for treatment, or for other purposes, doctors or other medical personnel need to sense various body potentials and in particular potentials in the heart area. Such potentials are normally sensed by placing an electrode in contact with or adjacent to the area being monitored and connecting the electrode through a wire to a terminal. Typically, a number of electrodes are mounted to a sensing probe or are bundled into a catheter, each electrode being connected by a separate wire to a separate connector element. The connector element may be, for example, a plug or a pin of a multi-pin connector.

The manufacture and assembly of such sensing devices has heretofore been a very labor-intensive operation and therefore quite costly. The discrete wires are soldered, welded or brazed to the electrodes and assembled into catheter shafts, fabric, mesh or rigid bodies. The manufacture and assembly of such sensing devices thus involves a large number of assembly steps, many of which require skilled and often artistic human execution. In addition to high cost, the large number of hand-performed steps can also result in small nonuniformities in finished products which can cause potentially catastrophic medical errors if such nonuniformities are not picked up during final testing. The requirements for numerous, sometimes difficult hand steps in the assembly operation of a single sensing device can also result in a significant scrap rate during manufacturing.

Further, since each discrete wire in such sensing devices normally has separate insulation, the size of the sensing devices and their mechanical characteristics such as stiffness, are directly affected by the number of sensing electrodes in the probe. Since such sensing devices are frequently catheters which are introduced into the heart through an artery, the size limitations imposed by the wires limits the number of sensing electrodes which can be utilized. Typically, such catheters cannot have more than four to six electrodes. Current construction techniques for the sensing devices limit the available spacing between electrodes so that it is difficult to manufacture a catheter which can simultaneously measure the potentials at closely adjacent points on the heart.

Another problem with the existing biopotential sensing catheters is that the size of the wires results in the wires taking up the full available space in the artery for the catheter. Thus, it is not possible to include a lumen with the catheter. A lumen is desirable with a catheter for the introduction of radio-opaque dyes to assist in guiding the catheter or for the introduction of medication or other substances useful in connection with a particular medical procedure.

The high manufacturing costs of existing sensing devices results in their being relatively expensive to purchase. However, in order to avoid contamination and to avoid using a catheter or other sensing device which has been damaged either in use or in sterilization, such devices are normally marketed as disposable devices adapted for only a single use. Nevertheless, in an effort to reduce expenses, hospitals frequently attempt to sterilize and reuse such devices. Such a practice poses a serious risk of contamination to the patient and of inaccurate readings as a result of using a sensing device which has been damaged. However, so long as such devices continues to be expensive, they will tend to be reused.

In an effort to reduce both the size and cost of such sensing devices, it has been proposed that printed circuit technology be utilized in their manufacture. Heretofore, some printed circuit sensors have been utilized for measuring skin potentials and other potentials on the body surface, and for measuring certain brain potentials or other potentials near the surface. Techniques have not been developed for utilizing such technology in connection with percutaneous catheters where the usable length of the catheter may be in the range of 125 centimeters, or with other sensing devices adapted for use in the heart or other deep internal organs where the connection between the electrodes and the connector terminals is relatively long.

It is therefore an object of this invention to provide biopotential sensing devices which are substantially less expensive to manufacture and assemble than existing such devices.

A further object of this invention is to provide biopotential sensing devices which take up far less space than existing such devices, permitting a greater number of contacts to be utilized, permitting such contacts to be closer together, and permitting a lumen to be utilized in conjunction with such devices when used as a percutaneous catheter.

A more specific object of this invention is to provide percutaneous catheters and other sensing devices designed for endocardial or other use deep in the body which are inexpensive enough to manufacture and assemble that hospitals will be willing to dispose of such devices after a single use rather than attempting to sterilize and reuse them.

A still more specific object of this invention is to provide biopotential sensing devices, and in particular percutaneous catheters and other endocardial sensing devices, or sensing devices for other deep body applications utilizing printed circuit technology.

SUMMARY OF THE INVENTION

In accordance with the above, this invention provides a biopotential sensing device which includes a thin film substrate and a predetermined printed circuit pattern formed on the substrate, the pattern having at least one electrode pad at its distal end, at least one terminal pad at its proximal end, and conductor means selectively interconnecting the electrode pads and the terminal pads. An elongated support member is also provided to which the substrate is secured in a suitable manner. In particular, the substrate is secured to the support member with the electrode pads and the terminal pads exposed, and with at least a portion of the substrate being wrapped around at least a portion of the support member. For a preferred embodiment of the invention, the support member is an elongated tube-shaped member having the substrate wrapped around it, the wrap preferably being helical. At least one lumen is preferably provided through the tube-shaped member and, for some embodiments of the invention, at least one of the electrodes is adapted for applying a potential as well as sensing a potential. In one embodiment of the invention, where the substrate is helically wrapped on a tube-shaped member, conductors are formed on only a selected fraction of the width of the substrate and the helical wrapping involves overlapping the portion of the substrate containing the conductors during the wrapping process. This permits the substrate to insulate and protect the conductor means and eliminates the need for a separate protective layer. The sensing device may either be a percutaneous catheter with the electrodes being formed at the distal end thereof, or may be a sensing probe which includes a sensing support member such as a solid plastic member or a balloon, which has the distal end of the substrate containing the electrode pads secured thereto.

The foregoing and other objects, features and advantages of the invention will be apparent from the following more particular description of preferred embodiments of the invention as illustrated in the accompanying drawings.

IN THE DRAWINGS

FIG. 1 is a side view of a percutaneous catheter of a preferred embodiment of the invention.

FIG. 2 is a rear view of the catheter shown in FIG. 1.

FIG. 3 is a top view of a printed circuit substrate suitable for use with the embodiment of the invention shown in FIG. 1.

DETAILED DESCRIPTION

Figure 4:
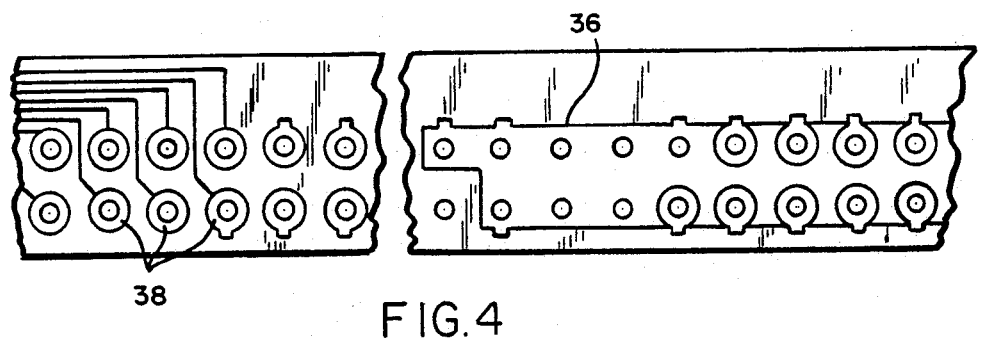
FIG. 4 is an enlarged view of the terminal pad portion of the printed circuit substrate shown in FIG. 3.

Referring to the figures, FIG. 1 shows a percutaneous catheter 10 having a distal end with a plurality of ring electrodes 12 and a proximal end having a molded bifurcated fitting 14. As will be discussed in more detail hereafter, the distal and proximal ends of the catheter are connected by flexible member 16 having tubing and circuitry. Fitting 14 has a strain relief 18 formed at its forward end over a portion of member 16, and has a first leg 20 which is formed over the rear tubing portion of member 16. Leg 20 has an opening 21 (FIG. 2) formed in its rear end which provides access to a lumen formed through the center of member 16. The other leg 22 of fitting 14 projects at an angle of, for example, 35° to leg 20, and has a of connector pins 24 extending therefrom.

For the embodiment of the invention shown in the figures, there are thirty-four pins 24. Legs 20 and 22 are connected by a supporting web 26.

Figure 8:
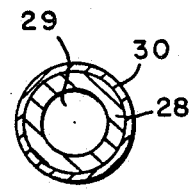
FIG. 8 is a cross section of the catheter shown in FIGS. 1 and 6 taken generally along the line 8—8 in FIG. 6.
Figure 7:
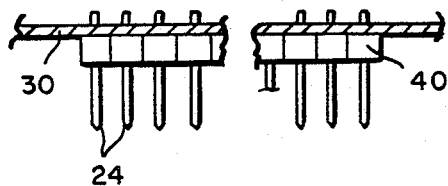
FIG. 7 is a view of the extended substrate portion of the subassembly shown in FIG. 6 taken generally along the line 7—7.
Figure 6:
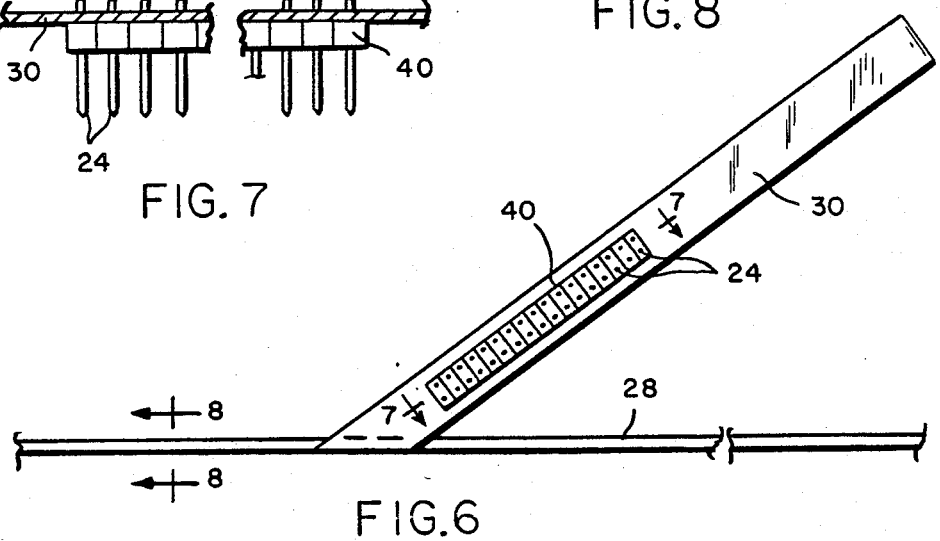
FIG. 6 is a side view of the rear or proximal portion of the catheter shown in FIG. 1 before a fitting is molded thereto.

Referring to FIGS. 6 and 8, the flexible member 16 is formed of a length of tubing 28 of woven dacron or other suitable material. A single lumen 29 is formed through tubing 28. The tubing may, for example, have an outer diameter of 0.05 inches and an inner diameter of 0.038 inches. The usable length of the tubing will vary with application. For a percutaneous transvenous catheter, the probe might have a usable length of 125 cm.

Helically wrapped around tube 28 is a polyimide plastic backing or substrate film 30 having a printed circuit formed thereon. The film substrate, which may, for example, be formed of Dupont Kapton, is very thin, having a thickness of less than 0.001 inches for preferred embodiments. Thicknesses of units of mils to tenths of mils are possible. The printed circuit pattern is formed on the substrate, utilizing one of a variety of known techniques. For example, a thin film copper foil could be laminated to the plastic film and the desired pattern generated on the film using standard photolithography techniques.

Figure 5:
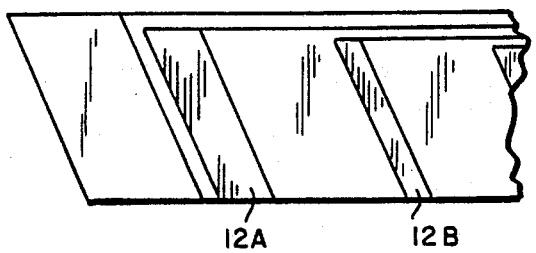
FIG. 5 is an enlarged view of two of the conductor pads of the printed circuit substrate shown in FIG. 3.

The printed circuit pattern on the film is best seen in FIGS. 3–5. From these figures it is seen that the pattern consists of eight electrode pads, 12A–12H, each of which is connected by a printed circuit wire 32 to a corresponding terminal pad 34. There are thirty four terminal pads 34, the eight forward ones of which are connected by the wires 32 to corresponding electrode pads 12. The remaining 26 terminal pads may be selectively interconnected as shown by the multipin terminal pad 36 (FIG. 4) to provide encoded information concerning the catheter. The coded multipin blocks may, for example, indicate the type or model of the sensor, the number of electrode pads, the configuration of such pads, or the like.

From FIG. 5, it is noted that the forwardmost one of the electrode pads, pad 12A, is somewhat wider than the remaining pads. For example, this pad might be 0.09 inches wide, while the remaining electrode pads are only 0.045 inches wide. Further, since the copper used for the printed circuit is not a biocompatible substance, the contact pads which are adapted to be in contact with the body are plated with a biocompatible metal such as gold or platinum. As will be discussed hereinafter, the remaining printed circuitry is covered so as not to be in contact with the patient's body.

In assembling the catheter of FIGS. 1–8, the desired printed circuit pattern is formed on substrate 30 and any required plating of electrodes or other printed circuit wiring is performed. In practice, a plurality of the patterns would normally be simultaneously formed on a large substrate sheet and the sheet then cut to form the individual substrates. A thermoset adhesive or a pressure-sensitive transfer adhesive is then applied to the film in standard fashion. The substrate 30 is then helically wrapped on tube 28. The angle of electrode pads 12, as seen in FIG. 5, is such that, when the substrate is helically wrapped on tube 28, the electrode pads form concentric ring electrodes. Since, as can be best seen in FIG. 3, wiring 32 is limited to the upper half of substrate 30, if the helical wrapping is performed with a roughly 50 percent overlap, the substrate on each successive wrap covers the wiring 32 from the preceding wrap. The substrate itself thus serves to cover and protect the wiring and prevent it from coming in contact with body tissue or fluids with which it is incompatible. This eliminates the need for an additional protective coating over the final flexible member 16, so that even with a 0.038 inch diameter lumen, the total diameter of the catheter can be as little as 0.065 inches. It has been found that the adhesive on the back of the film is sufficient to hold the film in place without an additional protective coating. However, if additional protective coating is desired, a dielectric coating of, for example, a silicone or polyurethane can be provided over the helically-wrapped substrate to further insulate and protect the substrate and wiring, and to assure that the helical wraps remain in place as the catheter is used. Such coating would increase the thickness of the catheter by an amount which varies with the coating untilized.

For a preferred embodiment, the helical wrap angle is approximately 35 degrees, resulting in the proximal end of substrate 30 projecting out at an angle of approximately 35 degrees from tubing 28 as shown in FIG. 6. Each terminal pad 34 has a hole 38 formed in it. A contact pin 24 is inserted in each hole 38 and the pins are wave-soldered to the terminal pads to assure physical and electrical connection between each pin and the corresponding terminal pad. To simplify assembly, pins 24 may be purchased as an assembly with the pins staked in block 40. The assembly may be mounted to substrate 30 in a single operation and wave soldered.

As a final step in the assembly operation, the fitting 14 is molded to the proximal portion of the tube 28 and substrate 30 to form the final configuration shown in FIG. 1.

Figure 9:
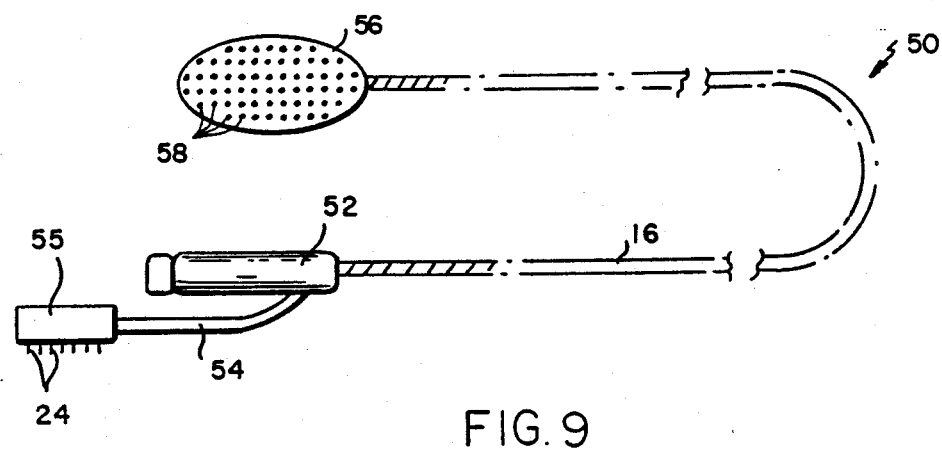
FIG. 9 is a side view of a probe embodiment of the invention.

FIG. 9 shows an alternative embodiment of the invention wherein the device is an interoperative probe rather than a catheter. The probe 50 has a flexible member 16 including the helically-wrapped printed circuit substrate, a fitting 52 at the end of the tubing 28 of member 16 providing access to the lumen therethrough, and a cable 54 to which the proximal end of the printed circuit wiring is connected, the cable leading to a connector block 55. Since cable 54 may have an axis which is substantially the same as the axis of member 16, this design, which may also be utilized with catheters of the type shown in FIG. 1, may enhance the maneuverability of the device since the cable 54 would not hinder movement as the more rigid angled interconnect of FIG. 1 might do.

The distal end of the probe has a probe element 56 to which the printed circuit electrode pads 58 on a printed circuit substrate of the general type shown in FIG. 3, but having a different geometry and a different printed circuit pattern, are attached. Element 56 will vary with application, but may, for example, be a solid plastic or hollow plastic component or a balloon which may be inflated through the lumen.

Figures 10, 11A, 11B:
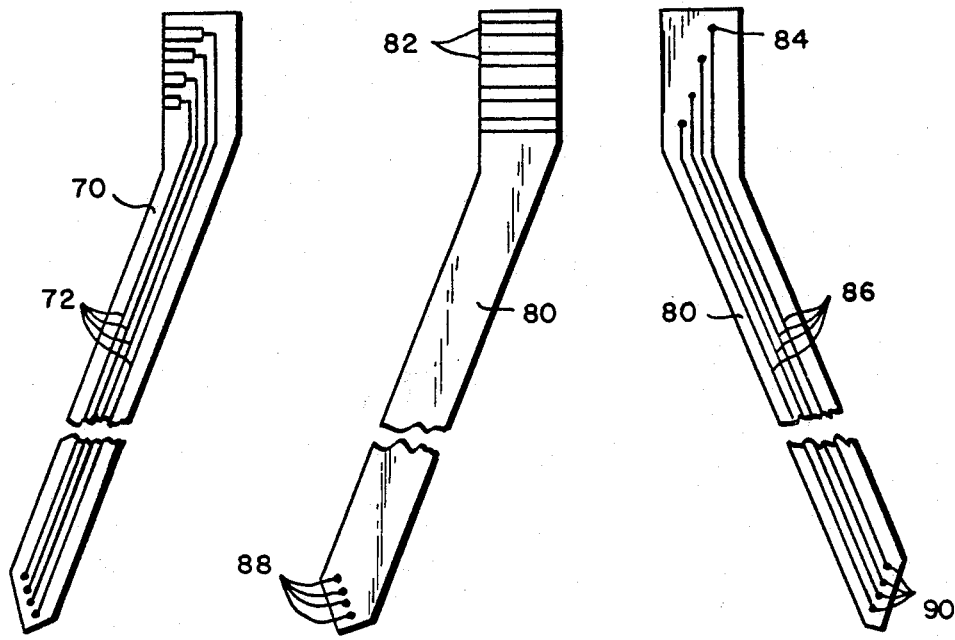
FIG. 10 is a top view of an alternative printed circuit substrate suitable for use in practicing the teachings of this invention.
FIGS. 11A and 11B are a top and bottom view, respectively, of a second alternative printed circuit substrate suitable for use in practicing the teachings of this invention.

FIG. 10 shows an alternative configuration 70 for the substrate and printed circuit wiring which differs from that shown in FIG. 3 primarily in that the electrodes are initially straight on the substrate rather than being angled, and the substrate itself goes off at an angle at a point just below the electrodes to permit the helical wrapping to be effected. The initial wrap with this substrate would be circular, followed by helical wraps. Since the wiring 72 on this substrate is not limited to roughly half the width thereof, it would be necessary to apply a protective coating over the substrate to insulate the wiring and prevent contamination resulting from the bioincompatibility of the wiring material.

FIGS. 11A and 11B show the top and bottom, respectively, of a printed circuit substrate 80 for another alternative embodiment of the invention. This substrate is similar to the substrate 70, but differs in that the contact pads 82 extend all the way across the substrate rather than only partially across the substrate, and have plated-through holes 84 formed therein which connect to printed circuit wiring 86 on the back surface of the substrate. The terminal pads 88 similarly have plated-through holes 90 formed therethrough which also connect to wires 86. With this configuration, if the contact pads 82 are plated with a suitable biocompatible metal, the remaining wiring can be wrapped against the tubing 28, the substrate 80 thus serving to insulate and protect the printed circuit wiring and avoid the need for an additional protective coating.

From the description above, it is apparent that, while for existing sensing devices, and particularly catheters, each increase in the number of contacts results in a corresponding increase in the number of wires and thus in the thickness and complexity of the device, the number of contacts with the sensing devices of this invention can be increased substantially without any corresponding increase in the size of the device. The principal limitation on the number of contacts is the number of printed circuit wires which can be fitted on the substrate. Existing substrates can accommodate at least sixteen wires on one side. Wider substrates and/or wiring on both sides on the substrate can increase the number of contacts which can be used. With the greater number of wires, it may be necessary to slightly increase the thickness of the device by adding a protective coating, since it may not be possible to lap over all of the wiring during the helical wrapping. However, with some slight increase in expense, it may be possible to eliminate the protective coating by utilizing the double-sided technique shown in FIG. 11. Utilizing this technique, either all of the wiring could be placed on the underside of the substrate, or enough wiring could be placed on the underside so that the remaining wiring could be lapped during wrapping. Since there is little if any extra cost in adding more terminals and wires with this invention, it might be possible to provide a standard probe or catheter with a larger number of contact pads and permit the user to selectively enable only such of the pads as are necessary for the user's application.

An additional advantage of this invention is that, using printed circuit technology, the electrodes can be spaced much closer together than is possible utilizing existing techniques. This permits a much more detailed mapping of biopotentials than is currently possible.

A related advantage is that the printed circuit technology permits the size, shape and orientation of each electrode to be individually controlled to provide a sensing device which is optimal for each application. The wiring and terminal pads may be similarly varied. The drawings show examples of some of these variations.

Another advantage of this invention is that most of the assembly steps can be mechanized, resulting in a sensing device which, even with an increased number of contracts, still is many times less expensive than existing devices. This should permit the devices to be priced at a level which will make it feasible for them to be truly disposable.

As previously indicated, at least one of the electrodes, for example electrode 12A, may be adapted for both applying potential and sensing potential. Thus, the device could be used for temporary pacing during cardiac catheterization, electrophysiology studies, cardiac surgery procedures, or other procedures where temporary pacing may be required. These electrodes could also be used for ablation. When so utilized, it may be desirable that the terminal pad only encircle a fraction of the circumference of flexible member 16 rather than being ring-shaped as shown in FIG. 1, so that energy is applied only to the spot where it is desired. Otherwise, the remainder of the electrode may be only heating blood, or possibly causing damage at points in the body other than the desired point. While the potential applying electrode has been shown in FIG. 5 as being wider than the sensing electrodes, this is the case for only a particular application and need not be done in all applications.

While the substrate has been shown as being helically wrapped above, it is apparent that other wrapping techniques or other means for securing the substrate to the tube 22 or other support member might be utilized. Further, while a number of printed circuit patterns have been shown for purposes of illustration, it is apparent that the particular printed circuit pattern utilized will vary with application. The nature of the support member for the printed circuit substrate will also vary with application and may, for certain applications, be a multi-lumen tube or a solid tube. The particular manner in which the printed circuit patterns are formed will also vary with application.

Thus, while the invention has been described above with respect to a number of embodiments, the foregoing and other changes in form and detail may be made therein by one skilled in the art without departing from the spirit and scope of the invention.

What is claimed is:

1. A biopotential sensing device comprising:
   a thin flexible substrate having a proximal end and a distal end;
   a predetermined printed circuit pattern formed on said substrate, said pattern having at least one electrode pad at its distal end, at least one terminal pad at its proximal end and conductor means selectively interconnecting said electrode pads and said terminal pads;
   an elongated support member; and
   means for mounting and securing said substrate to said support member, said means causing the covering of said conductor means while leaving said electrode pads and said terminal pads exposed.

2. A device as claimed in claim 1 wherein said support member is an elongated tube-shaped member; and
   wherein said means for mounting and securing includes means for wrapping said substrate around said tube-shaped member.

3. A device as claimed in claim 2 wherein said substrate is helically wrapped around the outside of said tube-shaped member.

4. A device as claimed in claim 3 wherein said conductor means are formed on only a selected fraction of the width of said substrate; and
   wherein said helical wrapping includes overlapping the portion of the substrate containing said conductor means during each helical wrap, whereby the substrate serves to insulate the conductor means.

5. A device as claimed in claim 3 wherein said electrode pads are formed at an angle to the conductor means such that, when said substrate is helically wrapped around said support member, said electrodes form concentric parallel rings around the support member.

6. A device as claimed in claim 2 including means for applying adhesive to the back of the substrate, the adhesive causing said substrate to be secured to said support member as it is wrapped thereon.

7. A device as claimed in claim 2 including at least one lumen formed through said tube-shaped member.

8. A device as claimed in claim 1 wherein at least one of said electrode pads is a means for both applying a potential and for sensing a potential.

9. A device as claimed in claim 1 wherein said device is of a given length which is sufficient to reach the heart or other organs deep within the body
   wherein said support member is an elongated tube-shaped member of substantially said given length; and
   wherein said means for mounting and securing includes means for wrapping the substrate around said tube-shaped member.

10. A device as claimed in claim 9 wherein said substrate is helically wrapped around said tube-shaped member.

11. A device as claimed in claim 9 wherein said tube-shaped member has at least one lumen formed therethrough.

12. A device as claimed in claim 1 wherein each of said terminal pads has a hole formed therein; and including a connector pin inserted in at least selected ones of said holes.

13. A device as claimed in claim 12 including means for physically and electrically connecting each connector pin to the associated terminal pad.

14. A device as claimed in claim 12 including means for selectively electrically connecting said terminal pads whereby encoded information concerning said device may be provided.

15. A device as claimed in claim 12 wherein said support member is an elongated tube-shaped member having a proximal end and a distal end;
   wherein said means for mounting and securing includes means for helically wrapping the substrate around said tube-shaped member, the portion of said substrate having said terminal pads printed thereon extending at an angle from a point near the proximal end of the tube-shaped member; and including
   at least one lumen extending through the tube-shaped member; and
   a bifurcated fitting molded to the proximal end of said tube-shaped member to provide access to said lumen and molded to the extending portion of said substrate and the connector pins to form an electrical connector for said device.

16. A device as claimed in claim 1 wherein said device is a sensing probe; and
   including a sensor support member, and means for securing the distal end of said substrate containing said at least one electrode pad to said sensor support member.

17. A device as claimed in claim 16 wherein said sensor support member is a solid plastic member having a predetermined shape.

18. A device as claimed in claim 16 wherein said sensor support member is a balloon.

19. A device as claimed in claim 1 wherein said predetermined printed circuit pattern is formed on both sides of said substrate, and wherein said printed circuit pattern includes means for interconnecting the patterns formed on each side.

20. A device as claimed in claim 19 wherein said means for interconnecting includes at least one plated through hole.

21. A method for fabricating a biopotential sensing device comprising the steps of:
forming a predetermined printed circuit pattern on a thin film substrate, the pattern having at least one electrode pad at a distal end of the substrate, at least one terminal pad at a proximal end of the substrate, and conductor means selectively interconnecting the electrode pads and terminal pads;
mounting the substrate to an elongated support member and securing the substrate thereto, said mounting and securing step involving wrapping at least a portion of the substrate around at least a portion of said elongated member, and being performed in a manner such as to cover said conductor means while leaving at least a portion of each electrode pad exposed at a distal end of the elongated member; and
utilizing the terminal pads to form a connector means, permitting the device to be connected to external circuitry.

22. A method as claimed in claim 21 wherein said mounting step includes helically wrapping said substrate about said elongated member.

23. A method as claimed in claim 22 wherein said conductor means are formed on only a selected fraction of the width of said substrate; and
wherein said helical wrapping step includes the step of overlapping the portion of the substrate containing the conductor means during each helical wrap, whereby the substrate serves to insulate the conductor means.

24. A method as claimed in claim 21 wherein said device is a sensing probe; and including the step of securing the distal end of the substrate containing the at least one electrode pad to a sensor support member.

* * * * *